(12) United States Patent
Czernik et al.

(10) Patent No.: US 8,636,939 B2
(45) Date of Patent: Jan. 28, 2014

(54) MOLD FOR ACTUATION SLED

(75) Inventors: Roman Czernik, Trumbull, CT (US); Steven Bartlett, Prospect, CT (US)

(73) Assignee: Covidien LP, Mansfield, MA (US)

( * ) Notice: Subject to any disclaimer, the term of this patent is extended or adjusted under 35 U.S.C. 154(b) by 549 days.

(21) Appl. No.: 12/259,629

(22) Filed: Oct. 28, 2008

(65) Prior Publication Data
US 2009/0115105 A1 May 7, 2009

Related U.S. Application Data

(60) Provisional application No. 60/985,666, filed on Nov. 6, 2007.

(51) Int. Cl.
  *B29C 45/37* (2006.01)
(52) U.S. Cl.
  USPC .................................. 264/328.8; 264/328.12
(58) Field of Classification Search
  USPC ............................... 264/328.12, 328.1, 328.8
  See application file for complete search history.

(56) References Cited

U.S. PATENT DOCUMENTS

| | | |
|---|---|---|
| 3,762,847 A | 10/1973 | Deuter et al. |
| 3,799,494 A | 3/1974 | McLean, Jr. |
| 3,889,919 A | 6/1975 | Ladney, Jr. |
| 5,087,193 A | 2/1992 | Herbert, Jr. |
| 5,324,186 A | 6/1994 | Bakanowski |
| 5,797,537 A | 8/1998 | Oberlin et al. |
| 5,834,035 A | 11/1998 | Osada et al. |
| 5,939,101 A | 8/1999 | Green |
| 6,367,765 B1 | 4/2002 | Wieder |
| 6,696,011 B2 | 2/2004 | Yun et al. |
| 7,134,637 B2 | 11/2006 | Dubay |
| 2004/0070205 A1* | 4/2004 | Thomas et al. ............... 285/307 |
| 2005/0006432 A1* | 1/2005 | Racenet et al. ............ 227/176.1 |
| 2005/0103819 A1* | 5/2005 | Racenet et al. ............ 227/175.1 |
| 2006/0068136 A1 | 3/2006 | Kinjou et al. |
| 2007/0075115 A1 | 4/2007 | Olson et al. |
| 2007/0194079 A1 | 8/2007 | Hueil et al. |
| 2008/0082124 A1 | 4/2008 | Hess et al. |
| 2008/0171168 A1* | 7/2008 | Matsuda ..................... 428/36.9 |

FOREIGN PATENT DOCUMENTS

| | | |
|---|---|---|
| DE | 3413113 A1 | 10/1984 |
| EP | 0931512 A | 7/1999 |
| EP | 1759812 A1 | 3/2007 |

(Continued)

OTHER PUBLICATIONS

European Search Report for EP 08253617.8-2307 date of completion is Mar. 10, 2009 (3 pages).

(Continued)

*Primary Examiner* — Jill Heitbrink

(57) ABSTRACT

An apparatus for injection molding includes at least one mold part having at least one surface. The mold part has at least one shaped portion. At least one substantially closed cavity region is disposed within the at least one surface. The one cavity region is designed for molding at least part of an interstitial mass. The apparatus further includes at least one gate disposed on the at least one surface for providing fluid communication to the at least one cavity region and at least one flow restrictor positioned on the mold part for initially directing flow of the interstitial mass to the at least one shaped portion. In one embodiment, flow restrictors initially direct the interstitial mass to an upper portion of the shaped portion.

12 Claims, 8 Drawing Sheets

(56) References Cited

FOREIGN PATENT DOCUMENTS

| EP | 1772105 | A1 | | 4/2007 |
|---|---|---|---|---|
| EP | 2058105 | A1 | | 5/2009 |
| WO | 2006/019068 | | * | 2/2006 |

OTHER PUBLICATIONS

European Search Report for EP 10251739.8-2307 date of completion is Dec. 29, 2010 (2 pages).

* cited by examiner

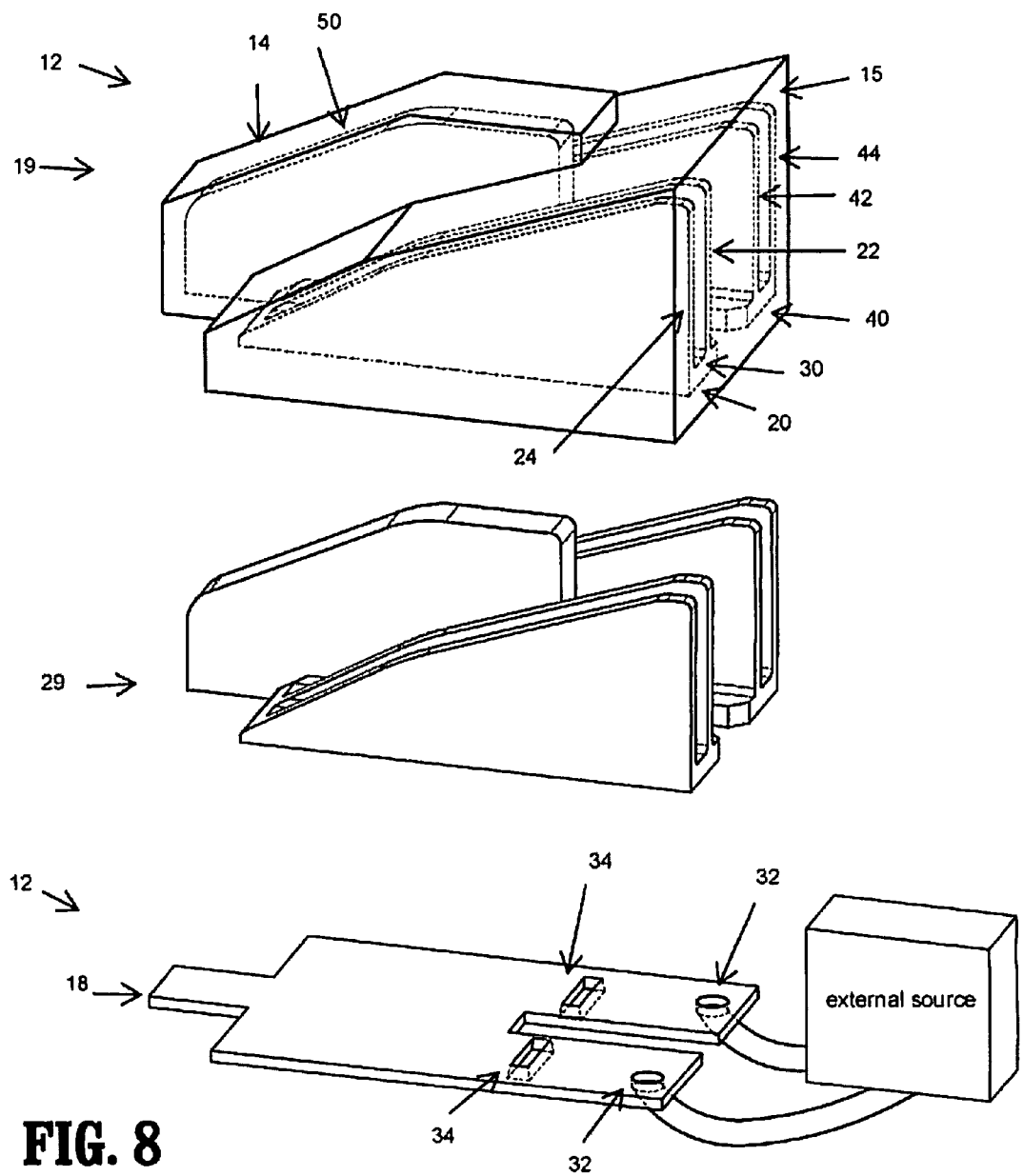

MOLD FOR ACTUATION SLED

CROSS-REFERENCE TO RELATED APPLICATIONS

This application claims the benefit of and priority to U.S. Provisional Patent Application No. 60/985,666 filed Nov. 6, 2007, the entire disclosure of which is incorporated by reference herein.

BACKGROUND

1. Technical Field

The present disclosure relates to a method, an apparatus and a system to manufacture an actuation sled and, more particularly, to a mold for injection molding of an actuation sled.

2. Background of Related Art

Injection molding is manufacturing process for producing parts and components. This process typically consists of inserting a molding material into an open rigid mold. The mold may be formed by halves. Typically, injection molding incorporates stationary and ejector mold halves, which open and close, to define a cavity where the molding or casting material is injected. Stationary mold halves are generally mounted to stationary platens. Ejector mold halves, in contrast, are capable of moving relative to stationary holder blocks for opening and closing the cavity. Ejector mold halves are mounted to ejector platens, which are generally connected to hydraulic actuators for providing movement. The stationary mold and the ejector mold are generally clamped together after the molding material has been inserted in the cavity. After a suitable curing cycle, the mold is separated from the formed product. A successful injection molding process produces a part or a product substantially shaped as the mold.

The injection molding process, however, does not necessarily produce flawless products. The quality of the manufactured product is occasionally compromised by shortcomings during the injection molding process. For instance, gas within the molding cavity can substantially diminish the quality of the final product. Vacuum assistance has been used to address this issue and improve product quality. The general purpose of the vacuum assistance is to improve the production of injection molding by removing gases from within the molding cavities. Ideally, vacuum assisted injection molding produces parts with a reduced level of porosity and greater physical characteristics.

The physical characteristics of a molded article can also be improved by positioning vents on the molds. These vents release gasses that otherwise would be trapped within the mold cavity. Consequently, vents reduce the occurrence of defective articles by minimizing incomplete mold cavity fillings.

Gases within the molding cavity are not the only cause of low quality products during the injection molding process. Occasionally, molding material is not uniformly distributed within the mold cavity. Therefore, there is a need for a method, system, and apparatus to evenly distribute molding material throughout the mold cavity during an injection molding process.

Medical devices manufacturers often employ injection molding to produce certain components of surgical instruments. For example, some parts of surgical staplers are manufactured using injection molding. In particular, actuation sleds can be made by injecting molding material into a mold cavity.

Actuation sleds serve to drive staple pushers vertically and, thus, eject staples. Actuation sleds typically include spaced apart ramps or cam wedges. These cam wedges are designed to cooperate with angular surfaces of the staple pushers to eject the staples. The angular surface of the staple pushers and the cam wedges complement each other.

The cooperation between the angular surfaces of staple pushers and the actuation sled is an important step of the surgical stapling process. Hence, actuation sleds should have cam wedges with the least amount of imperfections. It is thus desirable to develop an apparatus, system and method to manufacture a high quality actuation sleds.

SUMMARY

The present disclosure relates to an apparatus for injection molding. The apparatus includes at least one mold part having at least one surface. The mold part includes at least one shaped portion. At least one substantially closed cavity region is disposed within the surface of the mold part. The cavity region is designed for molding a cam member for a surgical stapler, the cavity region having an upper portion for forming a cam wedge. The presently disclosed apparatus further includes at least one gate on the surface. The gate provides fluid communication to the cavity region of the mold part. The apparatus additionally includes at least one flow restrictor positioned on the mold part for initially directing flow of the fluid to the shaped portion, the at least one flow restrictor being arranged to direct fluid toward the upper portion.

The at least one flow restrictor may be disposed on a lower surface of the mold part. In certain embodiments, the at least one flow restrictor comprises an indentation. The at least one mold part may be made of a polymer, or polyphtalamide. The at least one gate can provide fluid communication between the at least one cavity region and an external source of fluid or interstitial mass. In certain embodiments, the at least one shaped portion forms a plurality of cam wedges.

Another embodiment of the present disclosure relates to an apparatus for injection molding having at least one mold part. The mold part includes a surface encompassing a substantially closed cavity region, a shaped portion, and at least one gate disposed on the surface. The gate is configured to provide fluid communication to the cavity region. The apparatus also includes at least one flow restrictor positioned on the mold part for initially directing flow of the interstitial mass to the shaped portion.

In certain embodiments, the at least one shaped portion comprises an upper portion and a lower portion. The at least one flow restrictor may initially direct the interstitial mass to the upper portion of the at least one shaped portion. The at least one flow restrictor, in certain embodiments, is disposed on a lower surface of the mold part. The at least one flow restrictor can comprise an indentation. In certain embodiments, the at least one mold part is made of a polymer or polyphtalamide. The at least one gate may provide fluid communication between the at least one cavity region and an external source of fluid or interstitial mass. The at least one shaped portion, in certain embodiments, is formed by at least one cam wedge.

A method for manufacturing an actuation sled is also disclosed herein. The method comprises the steps of providing an apparatus having at least one mold part including a shaped portion, at least one gate, and at least one substantially closed cavity region. The method also entails introducing an interstitial mass into the substantially closed cavity region through the gate, initially directing the interstitial mass to the shaped portion, and solidifying the interstitial mass. In certain embodiments, the solidified interstitial mass is extracted from the apparatus. In certain embodiments, the cavity has an upper portion for forming a cam wedge. The mass may be initially directed toward the upper portion.

BRIEF DESCRIPTION OF THE DRAWINGS

Various embodiments of the presently disclosed apparatus will be described hereinbelow with reference to the drawings wherein:

FIG. 8 is a perspective view of a finished product molded by the apparatus illustrated in FIG. 1, showing the removal of the finished product from the apparatus illustrated in FIG. 1.

DETAILED DESCRIPTION OF THE EMBODIMENTS

Figure 1:
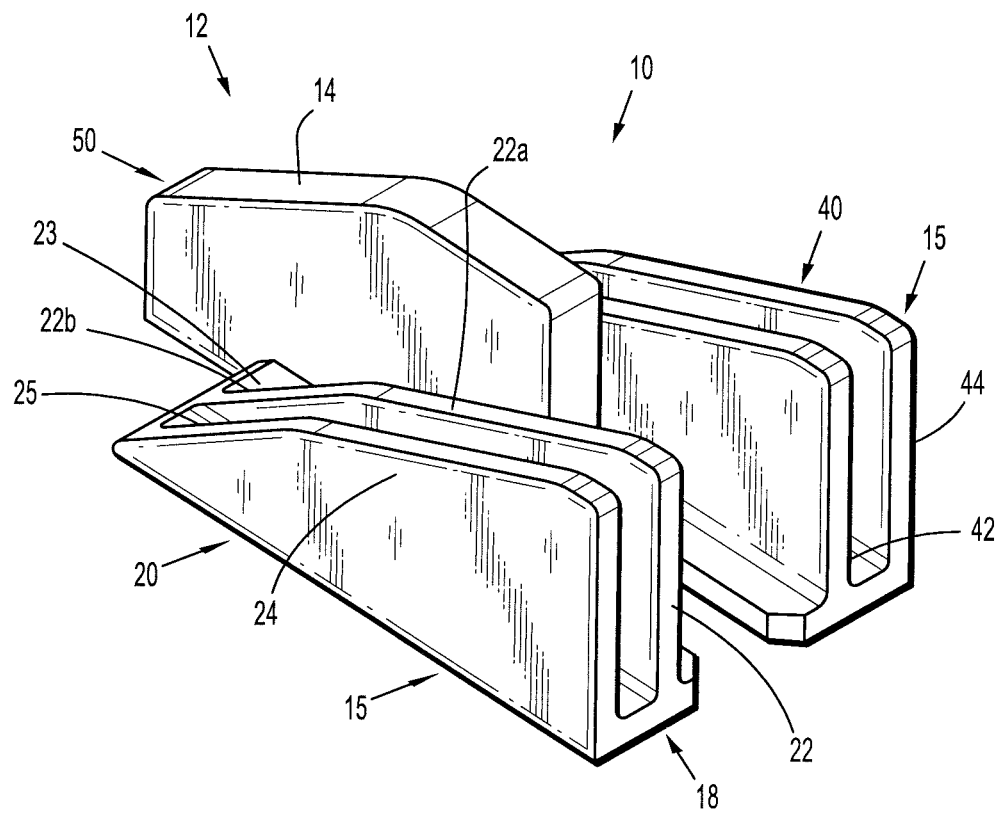
FIG. 1 is a perspective view of an apparatus constructed in accordance with an embodiment of the present disclosure.

The embodiments of the presently disclosed apparatus will now be described in detail with reference to the drawings in which like reference numerals designate identical or similar elements in each of the several views. As used herein and as is traditional, the term "distal" refers to the portion that is farthest from the user while the term "proximal" refers to the portion that is closest to the user. In addition, terms such as "above," "below," "forward," "rearward," "upper," "lower," etc. refer to the orientation of the figures or the direction of components and are simply used for convenience of description. As used herein a singular term generally includes the plural, and a plural term generally includes the singular unless otherwise indicated.

Injection molding typically entails the use of a mold. Most molds have a substantially closed cavity region. During the injection molding process, heated or melted molding material is introduced into the cavity region of the mold. This material should be rapidly injected to the cavity region at a substantially uniform and constant rate to inhibit premature curing of the material or incomplete filling of the molding cavity. The mold design should facilitate the flow of the molding material throughout the cavity region of the mold. The molding material should especially fill the essential sections of the mold.

Medical device manufacturers often use injection molding to make actuation sleds of surgical stapling instruments. Actuation sleds are typically used to drive staple pushers and thereby deploy staples disposed in a cartridge. Actuation sleds can include several shaped portions. For instance, a specific kind of actuation sled includes a base, a first camming member, a second camming member, and a guide member. First and second camming members may include respective first cam wedges and respective second cam wedges.

Molds used to make actuation sleds substantially mirror the shape of the sleds. Accordingly, a mold adapted to produce an actuation sled can include a base, first camming member, a second camming member, and a guide member. If the desired actuation sled has cam wedges, the mold should also have cam wedges.

Figure 2:
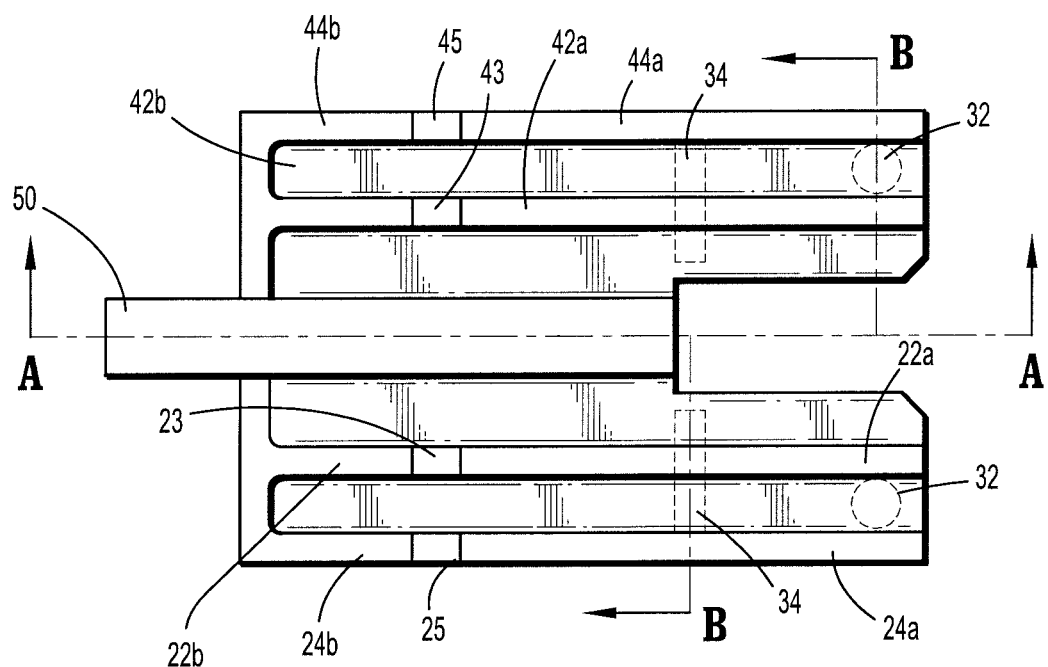
FIG. 2 is a top elevational view of the apparatus illustrated in FIG. 1.

Referring to FIGS. 1 and 2, an injection molding apparatus, according to an embodiment of the present disclosure, is shown generally as 10. The apparatus 10 includes at least one mold part 12 having at least one surface 14. Surface 14 defines the outer periphery of apparatus 10. The mold part 12 has at least one shaped portion 15 and can be made of a polymer such as polyphthalamide. Although the drawings depict a mold part 12 having specific kinds of shaped portions 15, the present disclosure envisions mold parts having shaped portion 15 with different shapes. The configuration of shaped portions 15 used with apparatus 10 is determined by the configuration of the finished product.

Figure 3:
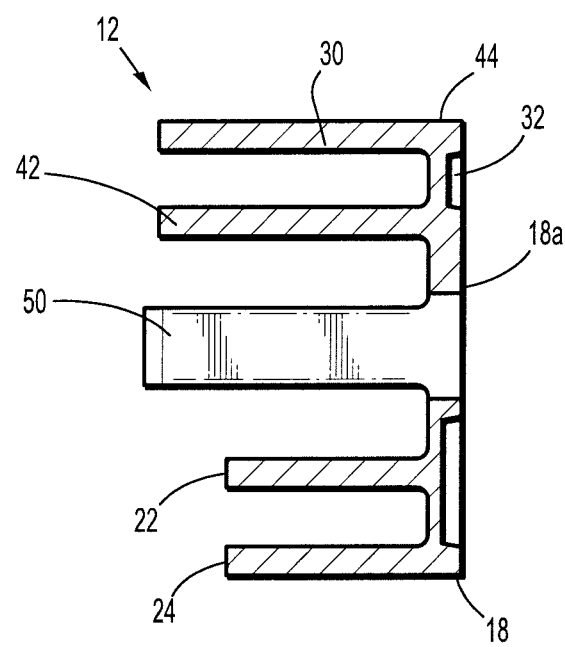
FIG. 3 is a rear cross-sectional view of the apparatus illustrated in FIG. 1, taken through section lines B-B of FIG. 2.

In the embodiment shown in FIG. 1, mold part 12 has a plurality of shaped portions 15. In particular, mold part 12 includes a base 18, a first camming member 20, a second camming member 40, and a guide member 50. Base 18 has a planar lower surface 18a (FIG. 3). It is contemplated, however, that lower surface 18a of base 18 may have other kinds of shapes, structures, and configurations. Irrespective of its shape, at least a portion of base 18 contacts first camming member 20, second camming member 40, and guide member 50.

Figure 5:
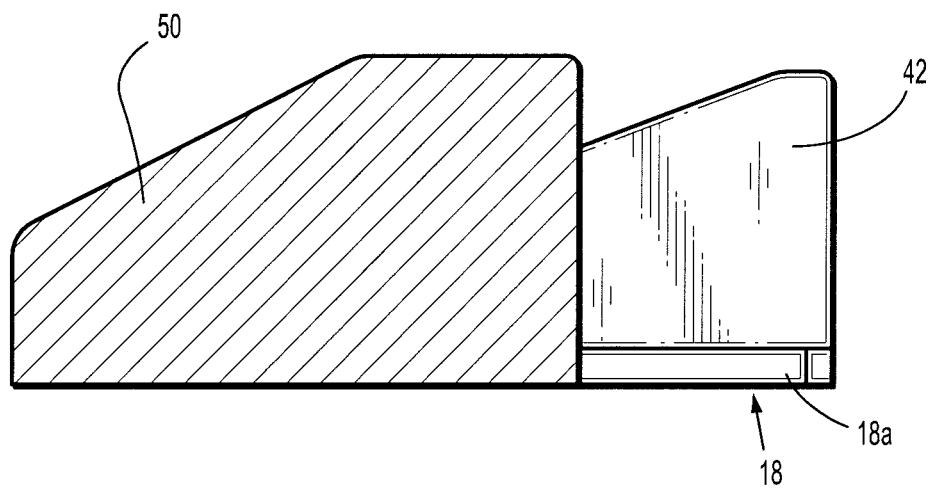
FIG. 5 is a cross-sectional view of the apparatus illustrated in FIG. 1; taken through section lines A-A of FIG. 2.

Guide member 50 is disposed between first and second camming members 20, 40 and is laterally spaced apart from camming members 20, 40. As seen in FIG. 2, a portion of guide member 50 extends longitudinally beyond the distal ends of camming members 20, 40. Additionally, guide member 50 extends vertically from base 18, as illustrated in FIG. 5. While the depicted embodiments show a guide member 50 having a particular spatial configuration with respect to base 18 and camming members 20, 40, the present disclosure envisions guide members having other suitable configurations. Ultimately, the configuration of guide member 50 is determined by the configuration of the finished product.

Figure 4:
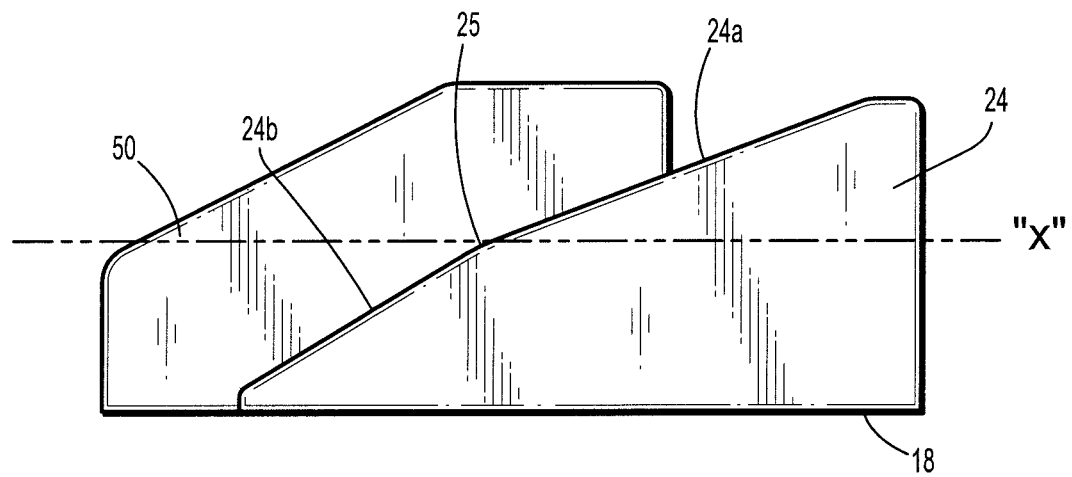
FIG. 4 is a side view of the apparatus illustrated in FIG. 1.
Figure 6:
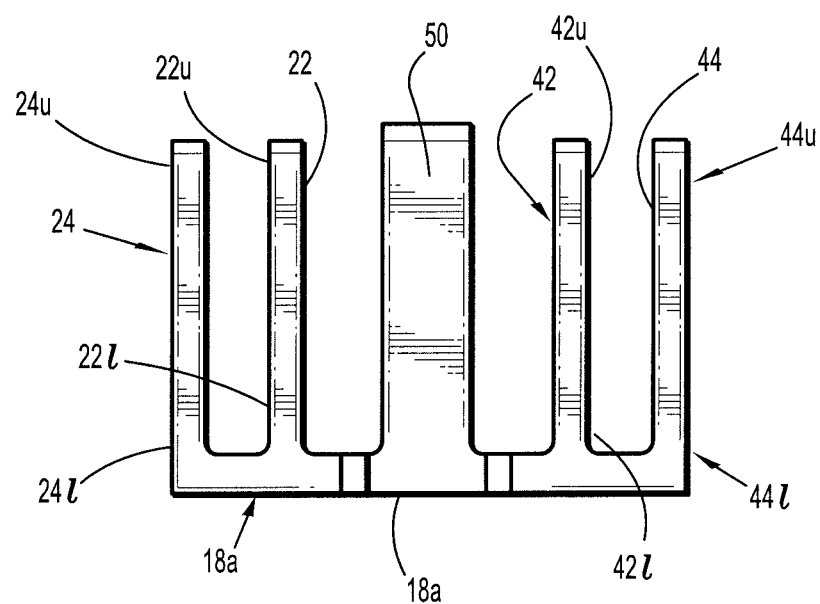
FIG. 6 is a rear elevational view of the apparatus illustrated in FIG. 1.

With reference to FIGS. 3-5, first and second camming members 20, 40 also extend vertically from base 18. Each camming member 20, 40 includes respective first cam wedge 22, 42 and second cam wedge 24, 44. Cam wedges 22, 24, 42, 44 have substantial triangular cross-sectional areas. The shapes of cam wedges 22, 24, 42, 44, however, ultimately depend on the desired shape of the cam wedges of the actuation sled. Thus, the present disclosure contemplates many other cam wedges having different shapes and sizes. As shown in FIG. 3, first cam wedges 22, 42 are laterally spaced apart from second cam wedges 24, 44, respectively. In addition, first cam wedges 22, 42 include respective upper portions 22u, 42u and respective lower portions 22l, 42l, as seen in FIG. 6. Similarly, second cam wedges 24, 44 include respective upper portions 24u, 44u and lower portions 24l, 44l.

With reference to FIG. 6, the upper portions 22u and 42u of first cam wedges 22, 42 include respective first drive faces 22a, 22b, 42a, and 42b. First drive faces 22a, 42a define first drive angles on camming members 20, 40 with respect to base 18 of apparatus 10. As seen in FIGS. 1, 2 and 4, transition points 23, 43 are disposed at the intersection of first and second drive faces 22a, 42a, and 22b, 42b, respectively. A plane X extending through transition points 23, 43 is substantially parallel to base 18. Second drive faces 22b, 42b define respective second drive angles on camming member 20, 40 with respect to plane X.

Similarly, second cam wedges 24, 44 include respective drive faces 24, 44 include respective first and second drive faces 24a, 24b, 44a, and 44b. First drive faces 24a, 44a define first drive angles on camming surfaces 20, 40 with respect to base 18. As seen in FIGS. 1, 2 and 4, transition point 25, 45 are positioned at the intersection of first and second drive faces 24a, 24b and 44a and 44b. Plane X extends through transition points 25, 45 and is substantially parallel to base 18. Second drive faces 24b, 44b define respective second drive angles on camming members 20, 40 with respect to plane X.

Figure 7:
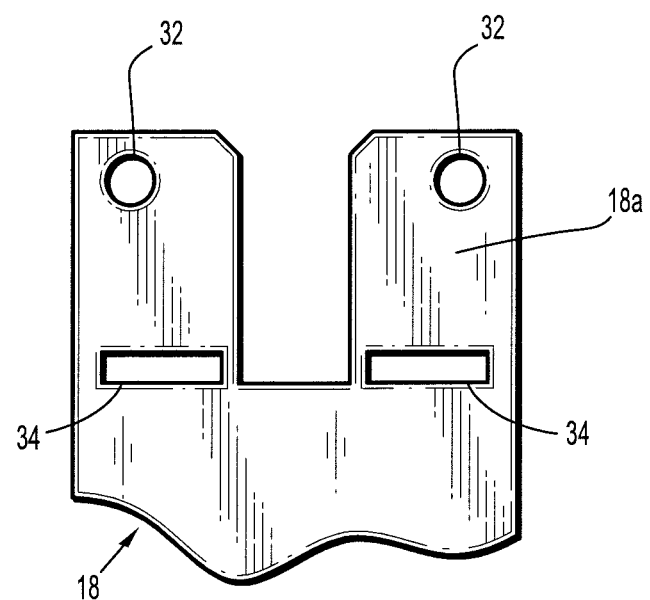
FIG. 7 is a bottom elevational view of the apparatus illustrated in FIG. 1.

With reference to FIGS. 3 and 6-7, the presently disclosed apparatus 10 further includes at least one substantially closed cavity region 30 disposed within the surface 14. Cavity region 30 is designed for molding at least part of an interstitial mass. The shape of cavity region 30 substantially mirrors the shape of the shaped portions 15 of mold part 12. Accordingly, in operation, the interstitial mass takes the shape of cavity region 30 to form an actuation sled or any other suitable product.

The interstitial mass is comprised by any suitable injection molding material. Thermoplastics, such as resins, polystyrene, polypropylene, polyethylene, polyvinyl chloride, polyetheretherketone, can be used as an injection molding material. During operation, the injection molding material is heated or melted and injected into cavity region 30 of mold part 12. Thereafter, the injection molding material solidifies to form the actuation sled or any other suitable part or component.

Referring to FIGS. 2-3 and 7, apparatus 10 includes at least one gate 32 on surface 14 for providing fluid communication to the cavity region 30 of mold part 12. In use, an external source of injection molding material supplies an interstitial mass to the cavity region 30 of the mold part 12 through gates 32. The embodiment shown in FIG. 2 has two gates 32 with circular cross-sectional areas. Gates 32, however, can have any suitable shape. In the depicted embodiment, gates 32 are disposed on the base 18 of mold part 12. Specifically, gates 32 are located on a proximal portion of base 18, as shown in FIG. 7.

Apparatus 10 additionally includes at least one flow restrictor 34 positioned on the mold part 12 for initially directing flow of the interstitial mass to the upper portion 22u, 24u, 42u, 44u of cam wedges 22, 24, 42, 44. Alternatively, flow restrictors 34 can be configured to direct the flow of interstitial mass to any other suitable shaped portion 15. In the illustrated embodiment, apparatus 10 includes two flow restrictors 34 longitudinally spaced apart from gates 32. Each flow restrictor 34 is disposed on the base 18 adjacent to a camming member 20, 40. The present disclosure, however, envisions that flow restrictors 34 can be positioned at any other suitable location. As depicted in FIG. 7, flow restrictors 34 have a substantially rectangular shape but other suitable shapes are also contemplated in the present disclosure. Each flow restrictor 34 can consist of an indentation. Regardless of flow restrictors 34 structure, flow restrictors 34 are adapted to direct flow of the interstitial mass to a shaped portion 15 of mold part 12. In doing so, flow restrictors 34 promote even distribution of the interstitial mass throughout cavity region 30. In one embodiment, flow restrictors 34 are specifically configured to initially direct flow of the interstitial mass to the upper portions 22u, 24u, 42u, 44u of cam wedges 22, 24, 42, 44. By initially directing flow to the upper portions 22u, 24u, 42u, 44u of cam wedges 22, 24, 42, 44, flow restrictors 34 facilitate uniform distribution of interstitial mass throughout cavity region 30. In use, the interstitial mass fills the upper portions 22u, 24u, 42u, 44u of cam wedges 22, 24, 42, 44 at the outset. Thereafter, the interstitial mass fills up the remaining portions of cavity region 30.

During the injection molding process, an external source of heated or melted injection molding material supplies cavity region 30 of mold part 12 with interstitial mass through gates 32. Gates 32, which are located at a proximal portion of base 18, provide the necessary fluid communication between the external source of injection molding material and cavity region 30 of mold part 12. As injection molding material is introduced into cavity region 30, flow restrictors 34 initially direct the material to the upper portions 22a, 24a, 42a, 44a of the cam wedges 22, 24, 42, 44. After the upper portions upper portions 22a, 24a, 42a, 44a of the cam wedges 22, 24, 42, 44 are filled with interstitial mass, the remaining space inside the cavity region fills with interstitial mass. Once a suitable curing cycle has elapsed, the interstitial mass solidifies. This solid mass can then be extracted from mold part 12.

As shown in FIG. 8, a top portion 19 of the mold part 12 can be separated from the base 18 to retrieve a molded product, namely, an actuation sled 29 from the cavity region 30 at the completion of the molding process. In their closed condition, the top portion 19 and the base 18 are mated together to define a closed cavity region 30 for molding the interstitial mass supplied by an external source through the gates 32. During the molding process, the closed cavity region 30 molds the interstitial mass into a shape of an actuation sled 29. At the completion of the molding process, the top portion 19 is separated from the base 18 to allow removal of the actuation sled 29 from the closed cavity region 30.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure. For example, it is contemplated that the shaped portions of the mold part may define the shape of another component of a surgical instrument.

What is claimed is:

1. A method comprising:
   injecting a fluid into a mold so as to form a guide member for a sled product, the mold being shaped so that:
   (i) the guide member has a proximal end and a distal end; and
   (ii) the guide member has at least one shaped portion;
   forming two gates with circular cross-sectional areas on a proximal portion of a base of the mold to receive the fluid; and
   forming two flow restrictors for directing flow of the fluid to the at least one shaped portion, the two flow restrictors longitudinally spaced apart from the two gates and disposed on the base of the mold adjacent to first and second camming members;
   wherein the two gates and the two flow restrictors facilitate uniform distribution of the fluid.

2. The method of claim 1, wherein the first and second camming members have first and second cam wedges, respectively.

3. The method of claim 2, wherein each of the first and second cam wedges includes at least first and second drive faces configured to define first and second drive angles with respect to a base portion of the sled product.

4. The method of claim 2, further comprising forming the first and second cam wedges as triangular cross-sectional areas.

5. The method of claim 1, wherein each of the two flow restrictors includes at least one indentation.

6. The method of claim 1, wherein the two flow restrictors have a substantially rectangular shape.

7. A method of forming a guide member for a sled product, the method comprising:

injecting a fluid into two gates with circular cross-sectional areas and formed on a proximal portion of a base of a mold;

forming two flow restrictors for directing flow of the fluid to at least one shaped portion, the two flow restrictors longitudinally spaced apart from the two gates and disposed on the base of the mold adjacent to first and second camming members; and solidifying the injected fluid;

wherein the guide member of the sled product is disposed between the first and second camming members; and wherein the two gates and the two flow restrictors facilitate uniform distribution of the fluid.

8. The method of claim 7, wherein each of the two flow restrictors includes at least one indentation.

9. The method of claim 7, wherein the first and second camming members have first and second cam wedges, respectively.

10. The method of claim 9, wherein each of the first and second cam wedges includes at least first and second drive faces configured to define first and second drive angles with respect to a base portion of the sled product.

11. The method of claim 7, wherein a portion of the guide member extends longitudinally beyond distal ends of the first and second camming members.

12. The method of claim 7, wherein the two flow restrictors have a substantially rectangular shape.

* * * * *